United States Patent [19]
Elson et al.

[11] Patent Number: 5,814,018
[45] Date of Patent: Sep. 29, 1998

[54] NEEDLE POINT GUARD SAFETY CAP ASSEMBLY

[75] Inventors: Edward E. Elson, Anaheim, Calif.; Lawrence R. Koh, 11755 Wilshire Blvd., 9th Fl., Los Angeles, Calif.

[73] Assignee: Lawrence R. Koh, Los Angeles, Calif.

[21] Appl. No.: 879,879

[22] Filed: Jun. 20, 1997

[51] Int. Cl.$^6$ ................................................. A61M 5/00
[52] U.S. Cl. ........................ 604/110; 604/192; 604/263
[58] Field of Search ................................... 604/110, 192, 604/198, 187, 263

[56] References Cited

U.S. PATENT DOCUMENTS

| | | | |
|---|---|---|---|
| 5,242,417 | 9/1993 | Paulder | 604/192 |
| 5,312,369 | 5/1994 | Arcusin et al. | 604/263 X |
| 5,348,544 | 9/1994 | Sweeney et al. | 604/192 |
| 5,700,249 | 12/1997 | Jenkins | 604/263 |

*Primary Examiner*—John D. Yasko
*Attorney, Agent, or Firm*—Gene W. Arant; Larry D. Baker

[57] ABSTRACT

A needle point cover assembly for securely covering and protecting the needle point after a syringe has been used includes a cover in the form of an elongated hollow member that is open at one end for receiving the needle therein, and at its other end is mostly enclosed by an end wall having a hole through which the needle can pass. A lid encloses the otherwise open end of the cover member. The lid has a hole through which the needle may pass so that the needle may extend through both the lid hole and the hole in the end wall. When the syringe is being used to make an injection, the needle point projects through the hole in the end wall. After an injection has been made and the syringe is ready for disposal, a manually actuable extensible frame slides the cover to where its end wall is beyond the extremity of the needle point. The cover member can then be supported by the hole in the lid and rotated about the lid hole until the needle point passes inside the enclosed end wall of the cover member into a protected position where it cannot pass through the cover member hole.

33 Claims, 9 Drawing Sheets

NEEDLE POINT GUARD SAFETY CAP ASSEMBLY

BACKGROUND OF THE INVENTION

The present invention relates to the field of hypodermic needles. More specifically, the present invention relates to the covering of a hypodermic needle point after use to prevent accidental sticks when disposing of the hypodermic needle.

Today, disposable hypodermic needles are an integral part of health care. Typical hypodermic needles include a replaceable plastic sheath which must be removed prior to use and subsequently replaced prior to disposal. The act of replacing the needle cap exposes the user, typically hospital or medical personnel, to accidental needle sticks.

An accidental needle stick can transmit diseases through the body's first line of defense-the skin. Because some diseases such as HIV are presently incurable and can ultimately lead to death, the exposed point of a used needle and every needle sheath replacement is potentially life threatening.

Although prior devices have addressed this problem, until now an effective and economical device has not been found.

SUMMARY OF THE INVENTION

According to the present invention a needle point cover assembly is provided that securely covers and protects the needle point after a syringe has been used.

The assembly preferably includes a cover in the form of an elongated hollow member that is open at one end for receiving the needle therein, and at its other end is mostly enclosed by an end wall having a hole through which the needle can pass. A lid typically encloses the otherwise open end of the cover member. The lid has a hole through which the needle may pass so that the needle may extend through both the lid hole and the hole in the end wall.

When the syringe is being used to make an injection, the needle point must project through the hole in the end wall. An extensible frame that is manually actuable can be attached to the cover member for moving the cover member along the needle when the syringe is being readied for disposal.

After an injection has been made and the syringe is ready for disposal, the cover is then slid to where its end wall is beyond the extremity of the needle point. The cover member can then be supported by the hole in the lid and rotated about the lid hole until the needle point passes inside the enclosed end wall of the cover member into a protected position where it cannot pass through the cover member hole.

DETAILED DESCRIPTION

With the needle point guard safety cap assembly of present invention, accidental needle sticks occurring after needle use can be virtually eliminated. To prevent accidental needle sticks, the present invention utilizes a cover or cap or cup-shaped member to cover or contain the point of the needle in a protected position after use.

The needle point cover has a hole so that it can be slid along the needle to a stowed position distal from the point prior to injection and then slid back along the needle to cover the point after injection. Once the point of the needle is within the cover after injection, the cover is rotated or skewed so that the needle point can not re-emerge through the hole in the cover.

The needle point cover is typically adapted to receive a typical needle sheath. As such, the needle point guard safety cap assembly typically can be installed prior to sheath installation and needle distribution. Needles can therefore be distributed with the needle point cover stowed distal the point and with the sheath covering the needle in the normal fashion.

In preparation for injection, the needle sheath is removed and the syringe is then used in the normal fashion to administer the injection. After injection, the needle point cover can be slid the length of the needle and rotated to prevent re-emergence of the needle point.

To facilitate rotation of the needle point cover and to provide a convenient means for sliding the cover along the needle, as well as to facilitate connection to a needle hub or syringe, the needle point guard safety cap assembly may also have a collapsible extension or extendible frame coupled to the needle point cover. The extension or frame can in turn be coupled to an attachment member which is adapted to attach to the needle hub in a non-releasable fashion. The needle hub in turn may be preassembled to a syringe, or a syringe may be attached to the needle hub prior to use in injecting or withdrawing fluids from a patient.

During sheath removal prior to injection, typically, the frame in co-operation with the attachment member, retains the needle point cover in its stowed position distal the needle point. After injection, the frame can be manually actuated or urged so that the needle point cover is released to slide toward and eventually cover the point.

After the point is contained within the cover, rotation can be made to occur in response to urging of the frame. Once the point of the needle is within the cover, further urging of the frame causes the cover to rotate. The rotated cover prevents the needle point from re-emerging through the hole in the cover.

To maintain the rotated position of the cover, the frame typically can be locked or secured to the needle shaft. Securing the frame also prevents the frame from collapsing and allowing the cover to slide back up the needle shaft which further ensures that the needle point can not be re-exposed.

Installation of the Presently Preferred Embodiment

The needle point guard safety cap assembly 100 of the present invention can be manufactured of a unitary molded plastic piece to increase reliability and to reduce manufacturing and installation cost. Although not required, the presently preferred embodiment of the present invention is of a unitary molded plastic piece. As a particular embodiment is not required to practice the invention, an alternate embodiment is also included to illustrate this.

The present invention is designed to be installed prior to needle use. It typically would be installed on the needle or syringe prior to distribution. The steps necessary to install the presently preferred embodiment are shown by the arrows in FIGS. 1–5.

To install the presently preferred embodiment of the needle point guard safety cap assembly, the syringe attachment member and the needle point cover must be rotated into position to receive the needle. The syringe attachment member and frame are flexibly coupled. The syringe attachment member or base cup 150 is therefore rotated approximately 90 degrees with respect to the frame 130 so that the needle can extend through the syringe attachment member 150 approximately parallel to the extended frame 130.

Next, a lid or enclosing member 118, which is flexibly coupled to the needle point cover 110, is rotated to plug or enclose the cover 110. The enclosed cover, which is flexibly coupled to the frame 130, is then rotated so that the needle can pass through both the hole in it and a hole in the syringe attachment member 150. As the cover is positioned to receive the needle, the frame or segmented extension 130 begins to collapse or fold at a flexible portion between the segments. The cover 110 is then slid along the needle shaft away from the needle point. To assist with this, as well as to position the cup-shaped member prior to needle insertion, the needle sheath 180 can be placed over the cover 110 in order to more easily manipulate the cover 110.

As the cover 110 is slid along the shaft, the frame or collapsible extension 130 continues to fold. As the cover closely approaches or contacts the needle hub or syringe, the frame 130 in co-operation with the syringe attachment member 150, releasably retains the cover. By using the sheath 180 to slide the cover 110 down the needle shaft, it too is installed in preparation for distribution. Sheath 180 removal prior to injection does not disturb the retained cover 110, however, the frame can be released by the user to actuate the cover.

The Presently Preferred Embodiment FIGS. 1–9

Figures 1, 2:
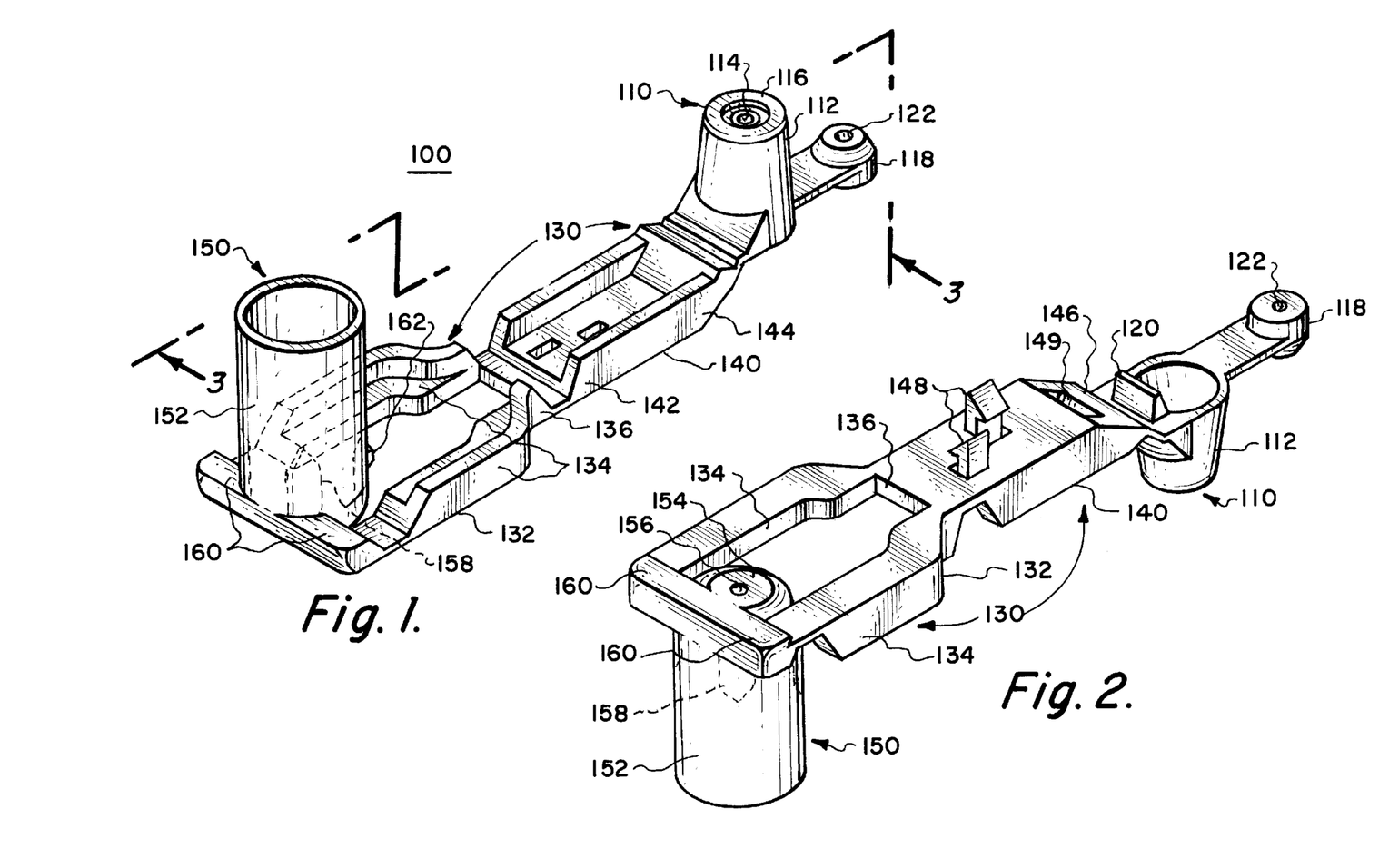
FIG. 1 is a perspective view of one side of the presently preferred embodiment of the needle point guard safety cap assembly.
FIG. 2 is a perspective view of the flip-side of the embodiment shown in FIG. 1.

FIGS. 1–9 illustrate one embodiment of the needle point guard safety cap assembly 100 of the present invention. It is presently preferred to form the needle point guard safety cap assembly of a unitary plastic piece. As such, FIGS. 1 & 2 depict alternate sides of the presently preferred needle point guard safety cap assembly as it appears after it is removed from a mold. FIGS. 3–9 depict the presently preferred embodiment as it is being prepared for use and in actual use with a syringe.

Turning to FIGS. 1 & 2, the needle point guard assembly or needle point cover 100 comprises the needle point cap or cup-shaped member or needle point covering means 110 for covering the point of the needle. The needle point cap or cover 110 is shaped in the form of an elongated member having a circumferential wall 112. One end of the elongated member 112 is open while the other is mostly enclosed by a bottom or end wall 116.

In the presently preferred embodiment of FIGS. 1 & 2, the hole or bore 114 in the bottom wall 116 of the needle point cap 110 allows the needle to pass through. A lever arm or rotating means 120 attached to the needle point cap, when urged, causes the needle point cap 110 to rotate about the needle point to prevent the needle point from passing through the hole 114.

FIGS. 1 & 2 show the enclosing member or top wall or lid 118 that is rotated about the needle point cap-to-enclosing member attachment so as to enclose the needle point cap 110. The enclosing member or enclosing means 118 has a bore or hole 122 to allow the needle to pass through. In this embodiment, the enclosing member or needle shaft engaging means 118 acts as a fulcrum which engages the needle. The fulcrum or needle shaft engaging means 118 engages the needle and provides a pivot point used for rotating the needle point cap when the needle is passing through enclosing member hole 122 but not through bottom wall hole 114.

In the embodiment shown in FIGS. 1 & 2, the needle point guard safety cap assembly 100 is adapted to be attached to the needle hub or syringe. The needle point cap 110 is coupled to the collapsible extension or collapsible member or collapsible segmented extension 130 which in turn is coupled to the syringe attachment member or base cup 150. The syringe attachment member 150 is used to connect the needle point guard assembly to the needle hub or syringe. In the presently preferred embodiment, the needle point cap 110 to collapsible member 130 coupling means is by direct coupling.

The base cup 150 has a circumferential wall 152 and a bottom wall 154. The bottom wall 154 has the hole 156 to allow the needle to pass through. In this particular embodiment, slats 158, which define channels in the inside of the circumferential wall 152 near the bottom wall 154, are included to allow for easy attachment of the base cup 150 to the needle hub. Also included in this embodiment are attachment arms 160 extending from the base cup 150 near the bottom wall 154. The attachment arms 160 are used to couple the base cup 150 to the collapsible member 130. The attachment arms 160 are flexibly connected to the collapsible member 130.

In the presently preferred embodiment the collapsible member or extensible frame 130 has many uses. It is used for connecting the syringe attachment member 150 to needle point cover 110 and for releasably securing the needle point cap 110 distal from the needle point. It is also used for sliding the needle point cover 110 down the needle shaft and facilitates rotation of the needle point cap 110 about the needle point. Additionally, it assists in maintaining the rotated position of the needle point cover 110.

The collapsible segmented extension 130, as shown in FIGS. 1 & 2, can be comprised of a wishbone segment 132 and a lower segment 140. The wishbone segment 132 has two arms 134 and a base 136. The wishbone arms 134 are flexibly connected to the base cup attachment arms 160. The wishbone segment base 136 is flexibly connected to the upper end 142 of the lower segment 140. A lower end 144 of the lower segment is flexibly connected to the needle point cap 110. The wishbone segment 132 forms an opening or means through which the clips 148 can extend when the collapsible segment 130 is folded. It also provides a means for allowing the locking surface 149 to contact the locking nub or protrusion 162 when the collapsible segment 130 is folded. This is more clearly shown in FIG. 6.

Figure 8:
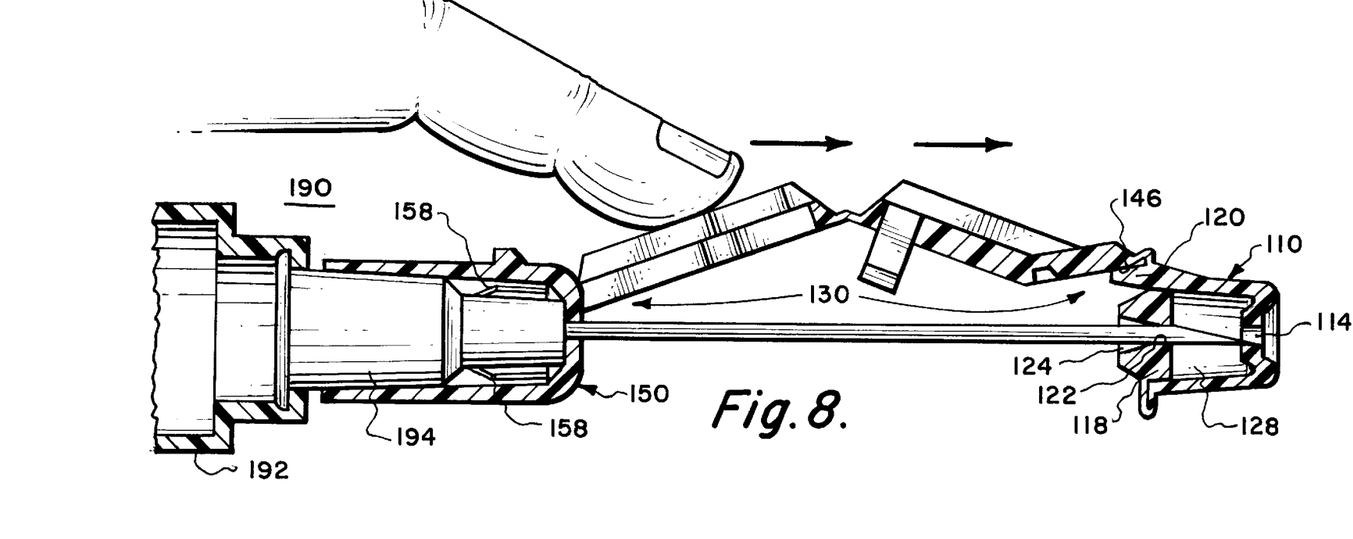
FIG. 8 is a cross-section of the presently preferred embodiment of FIG. 1 illustrating the needle point guard safety cap assembly attached to a syringe showing how the user actuates the assembly to cover the needle point.
Figure 9:
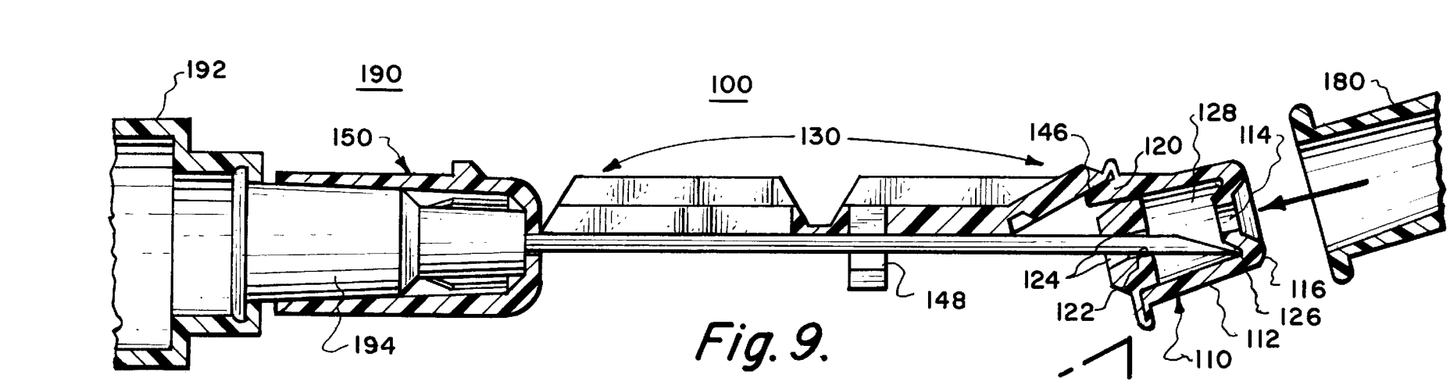
FIG. 9 is a cross-section of the presently preferred embodiment of FIG. 1 illustrating the needle point guard safety cap assembly attached to a syringe and depicting the rotated needle point cap covering the needle point and secured in a protected position after use.

FIG. 2 shows a pressure platform 146 that ultimately contacts the lever arm 120 and causes rotation of the needle point cap 110. Rotation of the needle point cap 110 about the needle point is best shown in FIGS. 8 & 9 and will be more thoroughly discussed later. Pressure platform 146 is adjacent locking surface or locking ledge 149. The locking surface 149 is used to secure the collapsible extension 130 to the base cup 150 when the extension is collapsed. The locking surface 149 will be discussed in more detail later.

FIG. 2 also shows a pair of protruding clips 148 that extend from the lower segment 140 to provide a protective position locking means. The clips 148 provide a means to secure the collapsible segmented extension 130 to the needle shaft after needle use. Securing the collapsible segmented extension 130 to the needle shaft ensures that the needle point cap 110 maintains its rotated or skewed position and also maintains the protective position of the needle point cap 110 so that it can not slide back up the needle shaft and expose the needle point. FIG. 9 shows one of the clips 148 engaging the needle shaft and securing the collapsible segmented extension 130 to the needle shaft.

Figure 3:
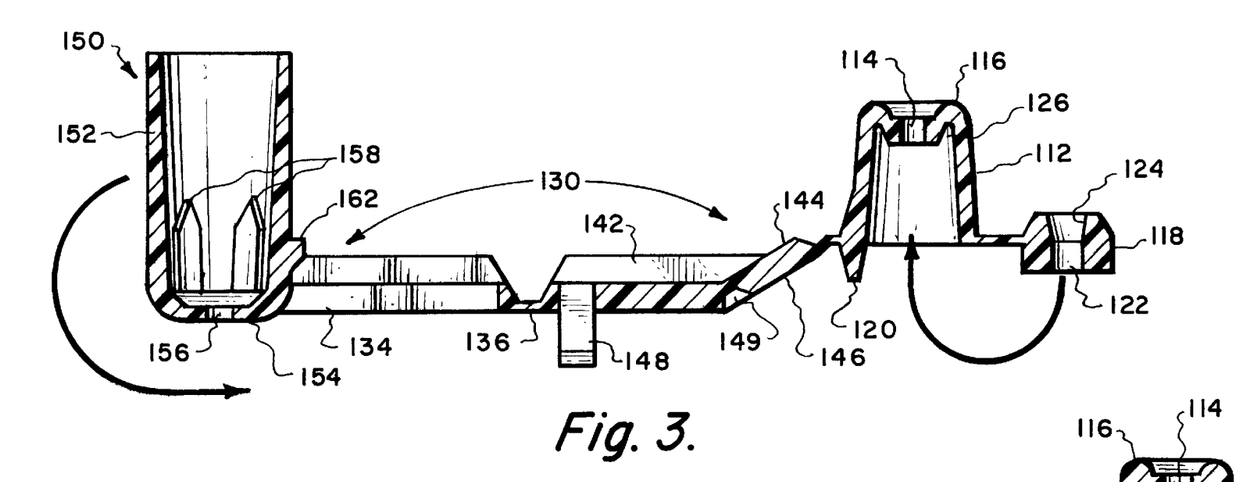
FIG. 3 is a cross-section at 3—3 of FIG. 1.
Figure 6:
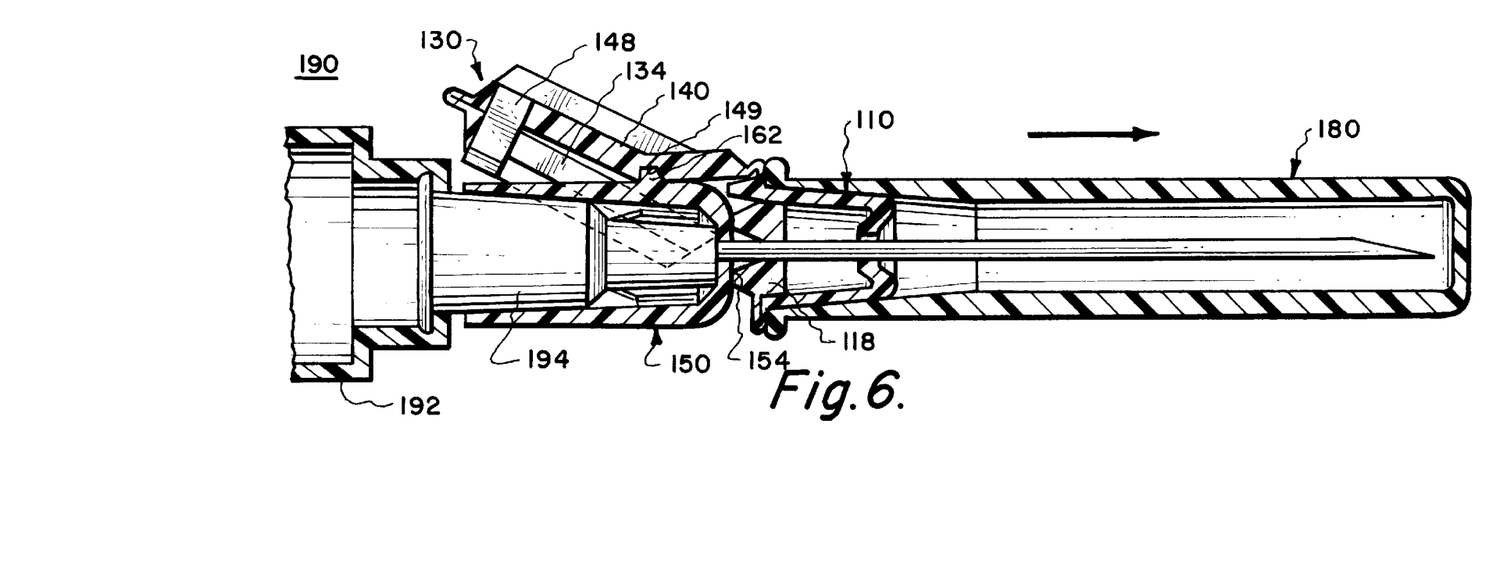
FIG. 6 is a cross-section of the presently preferred embodiment of FIG. 1 illustrating the needle point guard safety cap assembly attached to a syringe with a needle sheath covering the needle.
Figure 7:
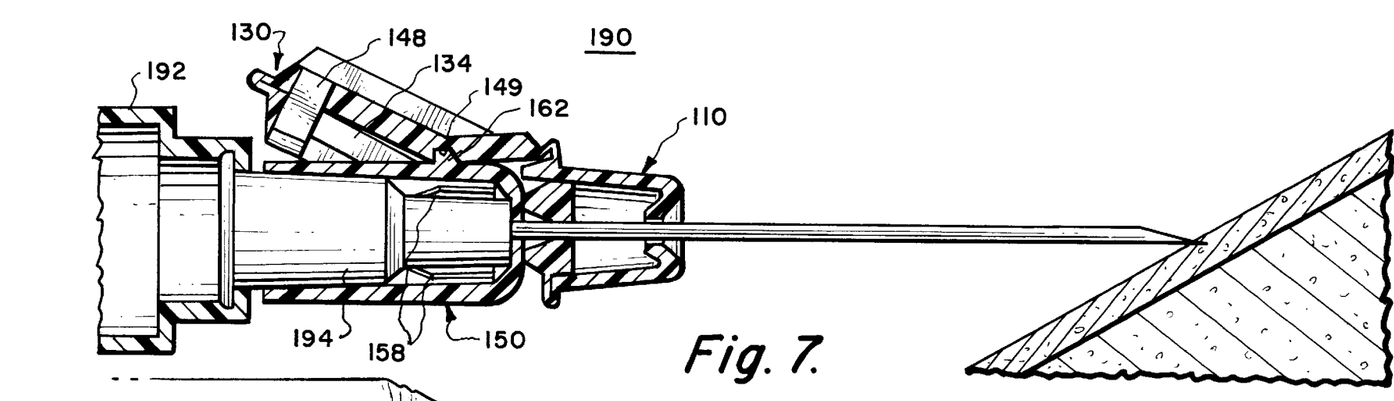
FIG. 7 is a cross-section of the presently preferred embodiment of FIG. 1 illustrating the needle point guard safety cap assembly attached to a syringe with the needle sheath removed so that the syringe is ready for use.

FIG. 3 shows how base cup 150 is rotated in preparation for needle passage through the base cup 150 and attachment to the syringe. The Slats 158 provide a means to orient and prevent rotation of the needle within the base cup when a syringe is attached to or separated from a needle seated in the base cup. The base cup or syringe attachment member 150 also has a protrusion or locking nub 162. The protrusion or locking nub 162 releasably engages the locking surface or locking ledge 149 to provide a locking means when the collapsible extension 130 is collapsed as shown in FIGS. 6 & 7.

Figure 4:
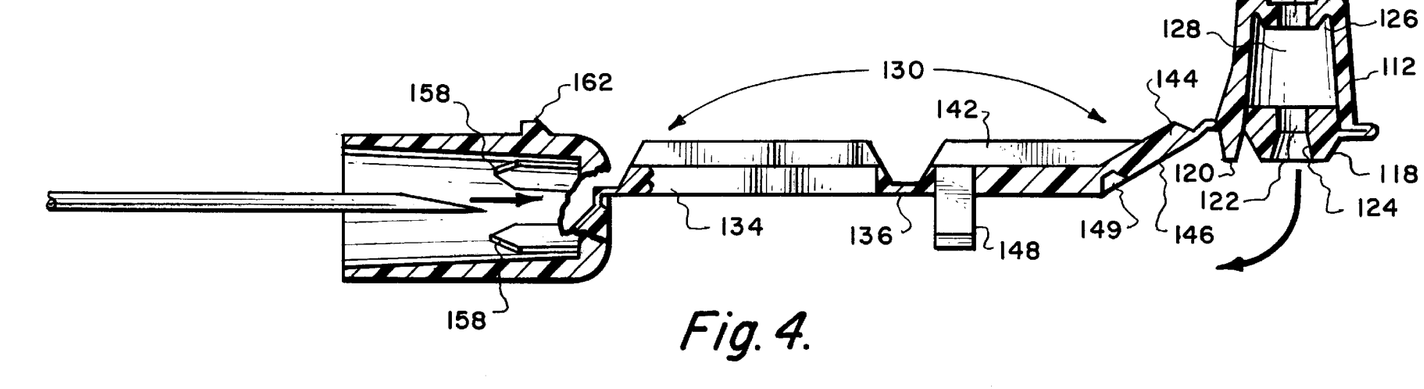
FIG. 4 is a cross-section at 3—3 of FIG. 1 when the needle point guard safety cap assembly is prepared for attachment to a syringe.

FIG. 3 also shows how the enclosing member 118 is rotated to enclose the needle point cap 110 to form a chamber 128 shown in FIG. 4. In the presently preferred embodiment, the hole or bore 122 in the enclosing member 118 has partially beveled edges 124. The partially beveled edges 124 allow the needle point cap 110 to more easily rotate about the needle point as is evident in FIG. 9.

In the preferred embodiment shown in FIG. 3, the needle point cap 110 has an annular channel 126 located around the hole or bore 114. It helps prevent the accidental re-emergence of the needle point through the hole 114 by capturing the needle point after the needle point cap 110 has been rotated about the needle point.

FIG. 4 depicts the base cup 150 after rotation and shows the direction of needle insertion in preparation for attachment of the needle point guard safety cap assembly 100 to the syringe. FIG. 4 also depicts the enclosed point cap 110 having the chamber 128. In this presently preferred embodiment, the chamber not only covers the point of the needle but also serves to capture fluid that might exude from the needle point.

The arrow adjacent the enclosed needle point cap 110 in FIG. 4 indicates the direction the enclosed needle point cap 110 is rotated in preparation for attachment of the needle point guard safety cap assembly 100 to the syringe. Rotation of the base cup 150 and the enclosed needle point cap 110 allows the needle to pass through both of them in preparation for attachment of the needle point guard safety cap assembly 100 to the syringe.

Figure 5:
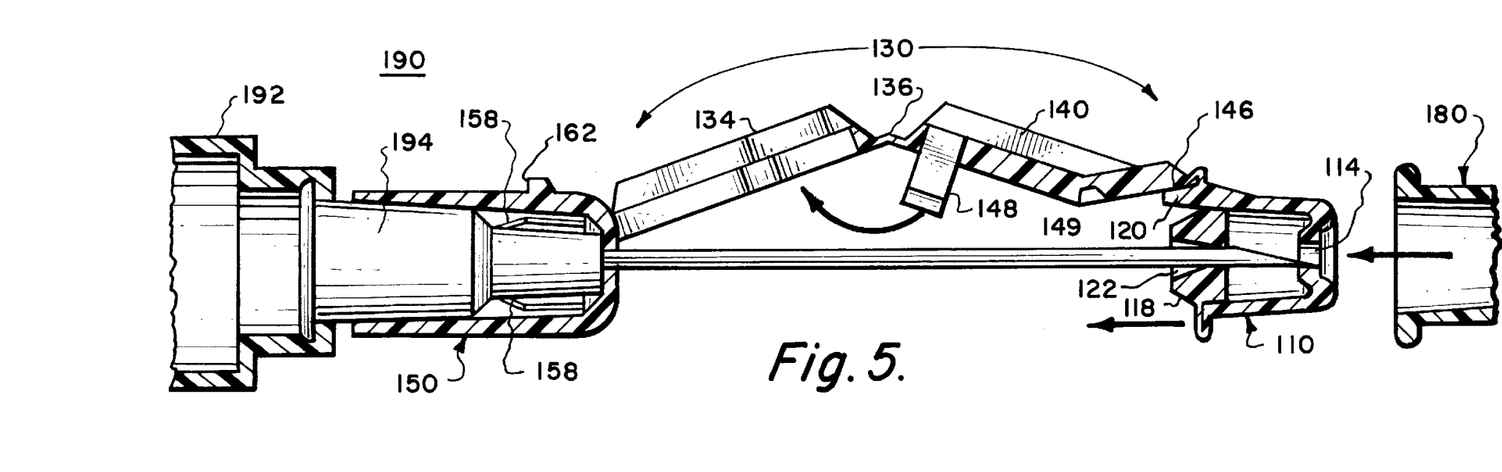
FIG. 5 is a cross-section of the presently preferred embodiment of FIG. 1 illustrating the needle point guard safety cap assembly attached to a syringe.

FIG. 5 depicts the needle point guard safety cap assembly 100 attached to the syringe 190 in preparation for receiving a needle sheath 180. Although in the presently preferred embodiment it is attached to the needle hub 194, it is also possible to attach it to syringe barrel 192 to provide a means for syringe 190 attachment.

As shown in FIG. 5, the collapsible extension 130 is beginning to collapse as the needle point guard safety cap assembly 100 is installed in preparation for application of needle sheath 180. FIG. 5, also shows how one of the clips 148 will ultimately extend between the arms 134 of the wishbone segment 132 when the collapsible extension 130 is collapsed. FIG. 6 shows the extension 130 collapsed or folded with one of the clips 148 extending between the arms 134 of the wishbone segment 132. Both of the clips 148, as is evident from FIG. 2, will extend between the arms 134 of the wishbone segment 132 when the collapsible extension 130 is folded.

FIG. 5 also depicts the base cup 150 locking nub or protrusion 162 and the locking surface or locking ledge 149 prior to needle sheath 180 application. The locking nub or protrusion 162 on the base cup 150 provides a surface to which the locking ledge or locking surface 149 on the collapsible extension 130 can contact to provide the means for releasable locking. The arms 134 of the wishbone segment 132 allow the locking nub 162 to contact the locking surface 149. FIG. 6 depicts the locking surface 149 engaging the locking nub 162 when the sheath is covering the needle.

As is evident from FIG. 6 the needle point cap 110 is adapted to receive the needle sheath 180 to protect the needle from contaminants prior to use. In the presently preferred embodiment, the enclosing member or top wall 118 abuts the bottom wall 154 of the base cup 150 to prevent needle contamination. The syringe with the needle point guard safety cap assembly 100 and the needle sheath 180 installed as depicted in FIG. 6, is as the user would receive it prior to use. To use the syringe, the user simply removes the needle sheath and proceeds to use the syringe in the normal manner depicted by FIG. 7. The engaged locking nub 162 and locking surface 149 keep the needle point cap 110 from sliding down the needle shaft while the needle sheath 180 is being removed.

Subsequent to use, the user simply urges the folded collapsible extension 130 with his finger to dislodge the locking surface 149 from the locking nub 162. The user then continues to urge the collapsible extension 130 to cause the needle point cap 110 to slide the length of the needle as shown in FIG. 8. In the presently preferred embodiment, as the needle point cap 110 nears the needle point, the pressure platform 146 nears and ultimately contacts the lever arm 120. After contact, further urging of the collapsible extension 130 causes a force to be applied to the lever arm 120. Approximately coincident with contact, the needle point clears the hole 114 and becomes located within the chamber 128. After the needle point has cleared the hole 114 the needle point cap 110 rotates about hole 122, and hence about the needle point in response to urging of the lever arm 120. FIG. 9 shows the rotated needle point cap 100.

As collapsible extension 130 approaches the needle shaft in response to the urging of the user, the clips 148 engage or surround the needle so that the collapsible extension 130 is clipped in place as shown in FIG. 9. This provides a means to maintain or secure the rotated position of the needle point cap 110 with respect to the needle point by maintaining engagement of the pressure platform 146 with the lever arm 120 so as to prevent the needle point from re-emerging through the hole 114. It also serves provides a means to keep the collapsible extension 130 from folding and allowing the needle point cap 110 to slide back up the needle shaft thereby exposing the needle point. Therefore, the clips 148 provide a means for securing the needle point cover 110 in the needle-protective position.

In addition, in the presently preferred embodiment depicted in FIG. 9, the annular channel 126 serves to capture the needle point and prevent it from re-emerging through the hole 114. The channel also helps to capture fluid that might exude from the needle point so that it can not easily escape from the needle point cap. It is also preferred to have the hole 122 closely surround the needle shaft so that fluid captured in the chamber, can not leak out through the hole 122. Furthermore, in preparation for disposal, needle sheath 180 can be placed over the needle point cap 110 for convenience and to ensure the capture of any excess fluid which might leak from the hole 114 in the bottom wall 116 of the needle point cap 110.

An Alternate Embodiment
FIGS. 10–16

Figure 10:
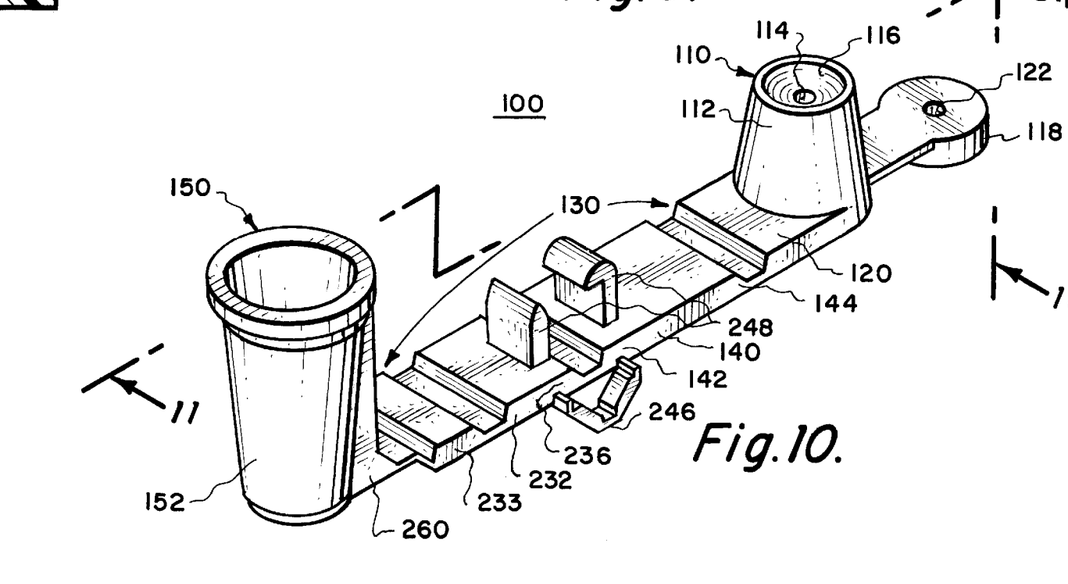
FIG. 10 is a perspective view of another embodiment of the needle point guard safety cap assembly.

FIG. 10 depicts an alternate embodiment of the invention formed of a unitary plastic piece. FIG. 10 depicts one side of the needle point guard safety cap assembly 100 as it would appear after it is removed from a mold. FIGS. 11–16 depict the alternate embodiment of FIG. 10 as it is to be prepared for use, and in actual use with the syringe.

In the alternate embodiment of FIG. 10, the needle point guard assembly 100 comprises the needle point cap or cup-shaped member 110 for covering the point of the needle. The hole or bore 114 in the bottom wall 116 of the needle point cap 110 allows the needle to pass through. The lever arm 120 attached to the needle point cap, when urged, causes the needle point cap 110 to rotate about the needle point to prevent the needle point from passing through the hole 114.

An enclosing member or top wall 118 is rotated about the needle point cap-to-enclosing member attachment so as to enclose the needle point cap 110. The enclosing member 118 has the bore or hole 122 to allow the needle to pass through. In this embodiment, the enclosing member or needle shaft engaging means 118 acts as the fulcrum which engages the needle. The fulcrum or needle shaft engaging means 118 engages the needle and provides the pivot point used for rotating needle point cap when the needle is passing through enclosing member hole 122 but not through bottom wall hole 114.

In the alternate embodiment shown in FIG. 10, the needle point guard safety cap assembly 100 is adapted to be attached to the syringe hub. The needle point cap 110 is coupled to the collapsible member or collapsible extension or collapsible segmented extension 130 which in turn is coupled to the base cup or syringe attachment member 150 for connecting the needle point guard assembly to the syringe.

The base cup 150 has the circumferential wall 152 and the bottom wall 154. The bottom wall 154 has the hole 156 to allow the needle to pass through. Included in this embodiment is a rigid portion 260 extending from the base cup 150 near the bottom wall 154. The rigid portion 260 is used to couple the base cup 150 to the collapsible member 130. The rigid portion 260 is flexibly connected to the collapsible member 130.

The collapsible segmented extension 130, as shown in FIG. 10, can be comprised of an upper segment 232 and the lower segment 140. The upper end 233 of upper segment 232 is flexibly connected to the rigid portion 260. The lower end 236 of the upper segment 232 is flexibly connected to the upper end 142 of the lower segment 140. The lower end 144 of the lower segment 140 is coupled to the needle point cap 110. This coupling means is by way of direct attachment of the lower segment 140 to lever arm 120, which in turn is attached to needle point cap 110.

Figures 15, 16:
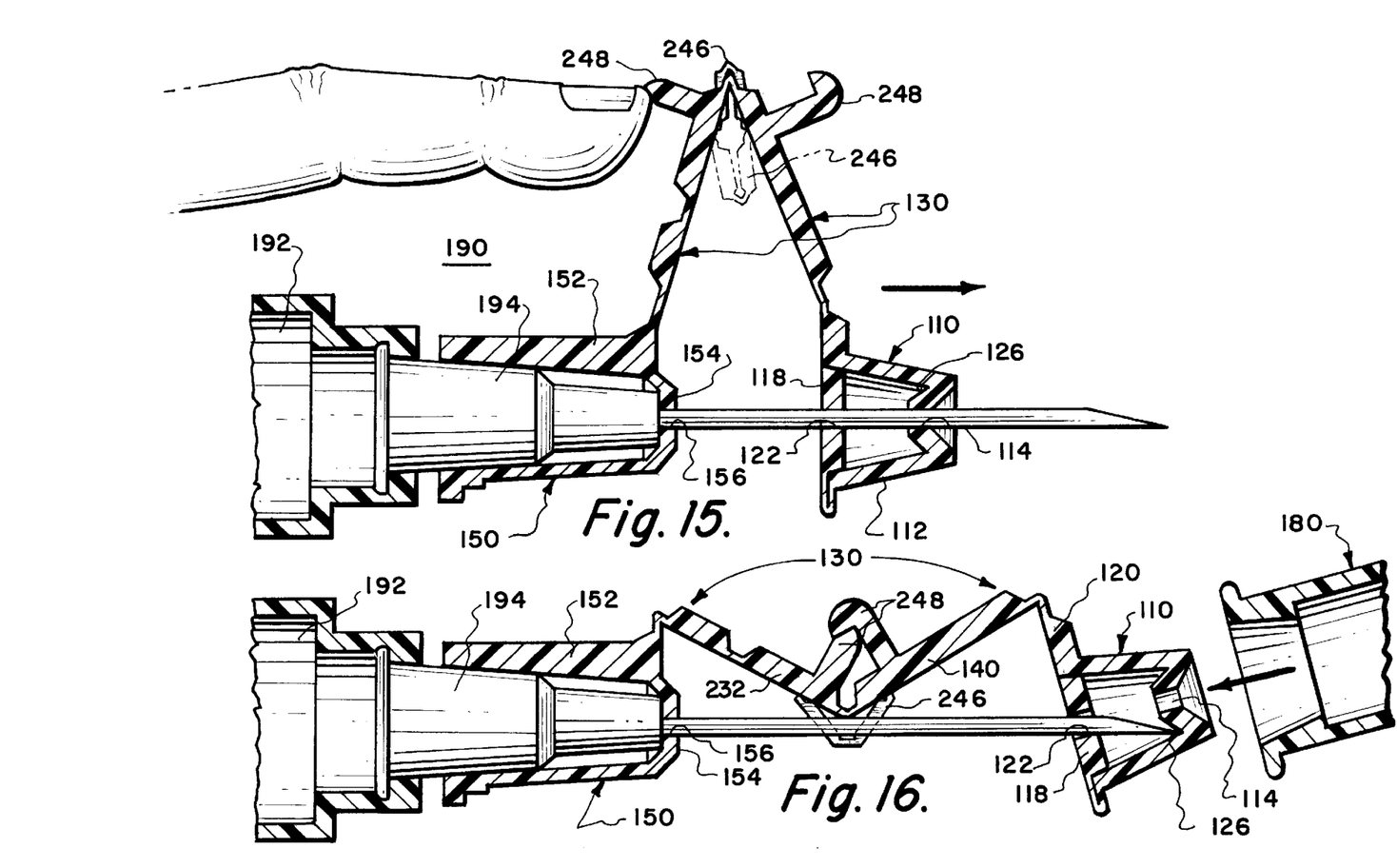
FIG. 15 is a cross-section of the alternate embodiment of the needle point guard safety cap assembly of FIG. 10 attached to the syringe
FIG. 16 is a cross-section at 11—11 of FIG. 10 illustrating the rotated needle point cap locked in a protected position.
Figure 17:
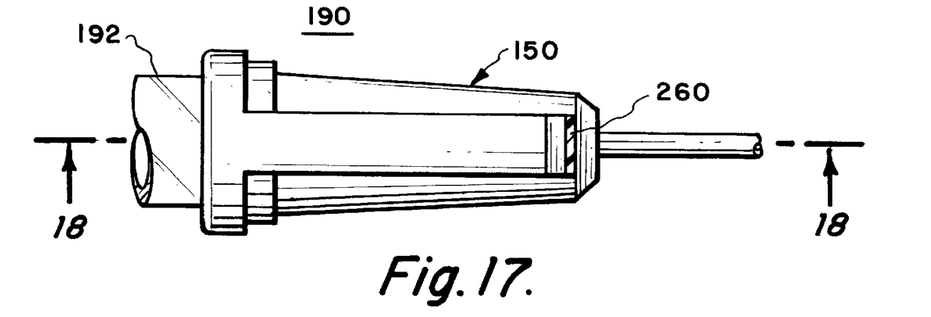
FIG. 17 is a view of the alternate embodiment of FIG. 10 showing only the syringe attachment member.
Figure 18:
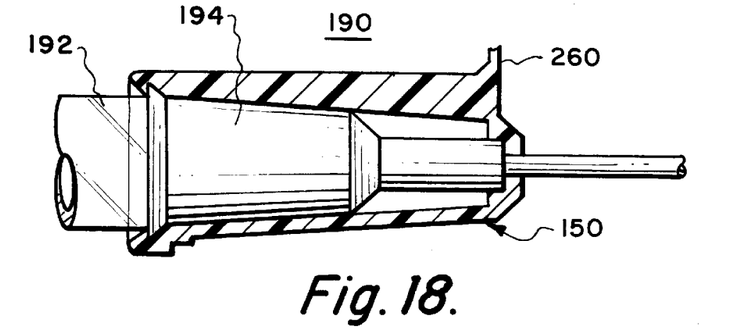
FIG. 18 is a cross-section at 18—18 of FIG. 17 illustrating the syringe attachment member attached to the syringe.
Figure 19:
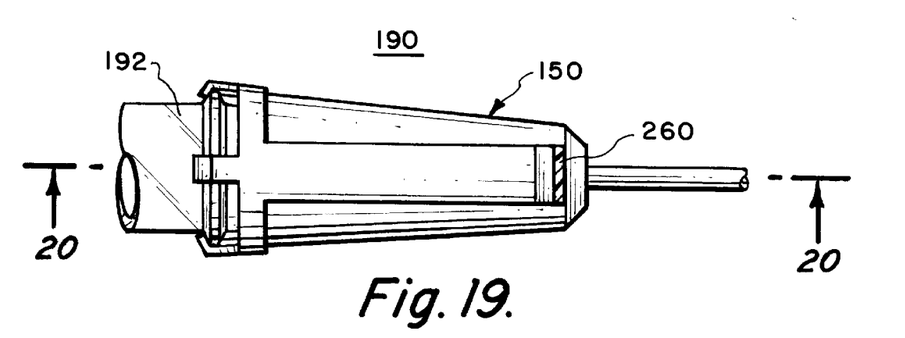
FIG. 19 is and alternate embodiment of the syringe attachment member.
Figure 20:
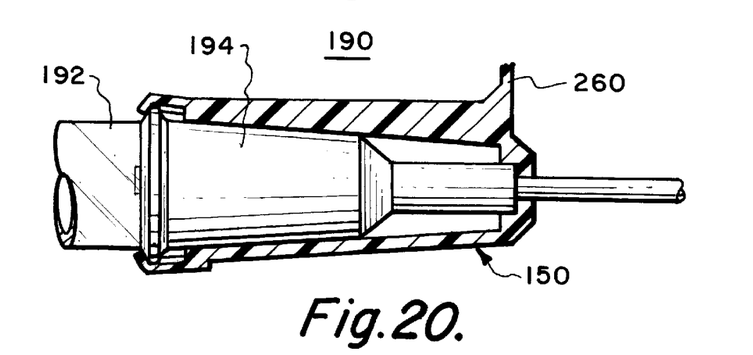
FIG. 20 is a cross-section at 20—20 of FIG. 19 illustrating the syringe attachment member attached to the syringe.

FIG. 10 also shows a pair of interlockable protrusions 248. One of the protrusions 248 extends from upper segment 232 while the other extends from the lower segment 140. The interlockable protrusions 248 provide the protective position locking means to maintain the position of the needle point cap 110 so that it can not slide back up the needle shaft and expose the needle point and to ensures that the needle point cap 110 maintains its rotated or skewed position. FIG. 16 shows the protrusions 248 interlocked. Alternatively, a clip or engaging means could be used to secure the collapsible extension 130 to the needle shaft to prevent its movement after use.

Figure 13:
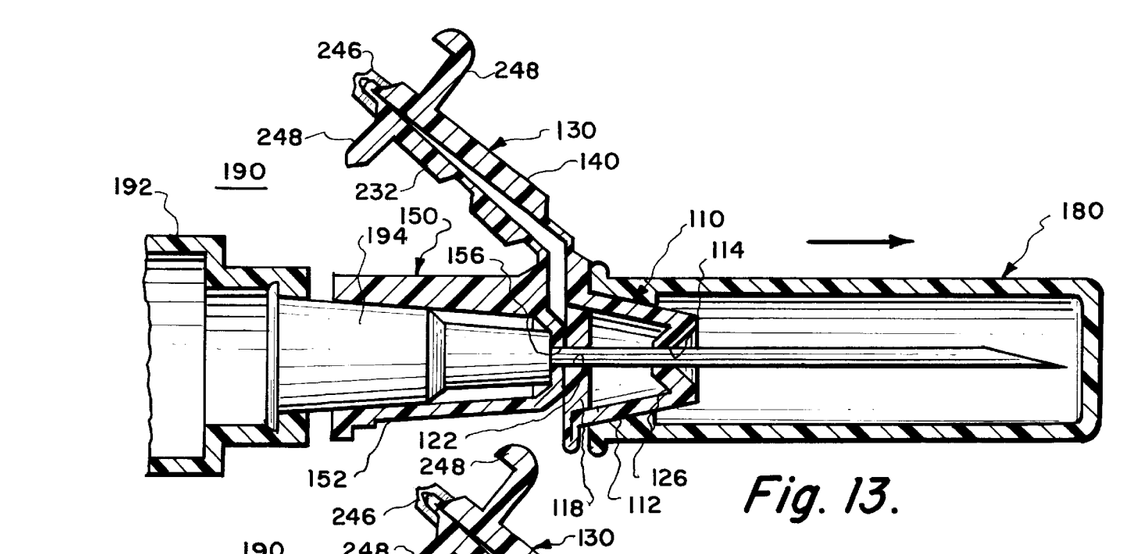
FIG. 13 is a cross-section of the alternate embodiment of the needle point guard safety cap assembly of FIG. 10 attached to the syringe with a needle sheath covering the needle.
Figure 14:
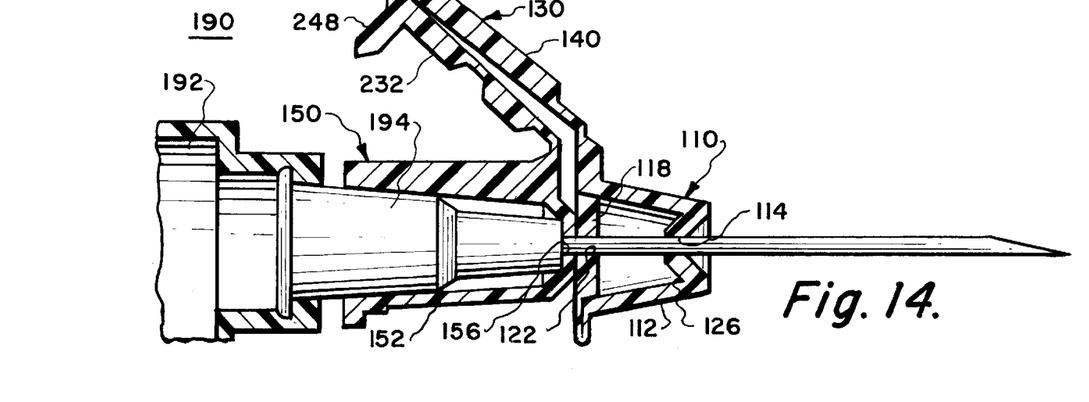
FIG. 14 is a cross-section of the alternate embodiment of the needle point guard safety cap assembly of FIG. 10 attached to the syringe after removal of the needle sheath.

Also in the alternate embodiment of FIG. 10, a snap-lock 246 provides a means to releasably lock the collapsible extension 130 when the collapsible extension is folded and thereby releasably lock the needle point cap 110 is in a position distal from the point. The snap-lock 246 snaps into its locking position as the collapsible extension 130 is collapsed. FIGS. 13 & 14 show the snap-lock 246 releasably locking or securing the collapsible extension and thereby releasably locking the needle point cap 110 distal the needle point. Urging of the collapsible extension 130 causes the snap-lock 246 to snap to release the collapsible extension 130 and allow the needle point cap 110 to be slid down the needle as shown in FIG. 15. FIG. 15 shows the snap-lock 246 just prior to snapping and, in phantom, just after snapping to release the collapsible extension 130.

Although the snap-lock 246 is shown extending from opposite sides of the collapsible extension 130, it could be located between the upper and lower segments of the collapsible extension 130 so that it does not stick out from either side.

Figure 11:
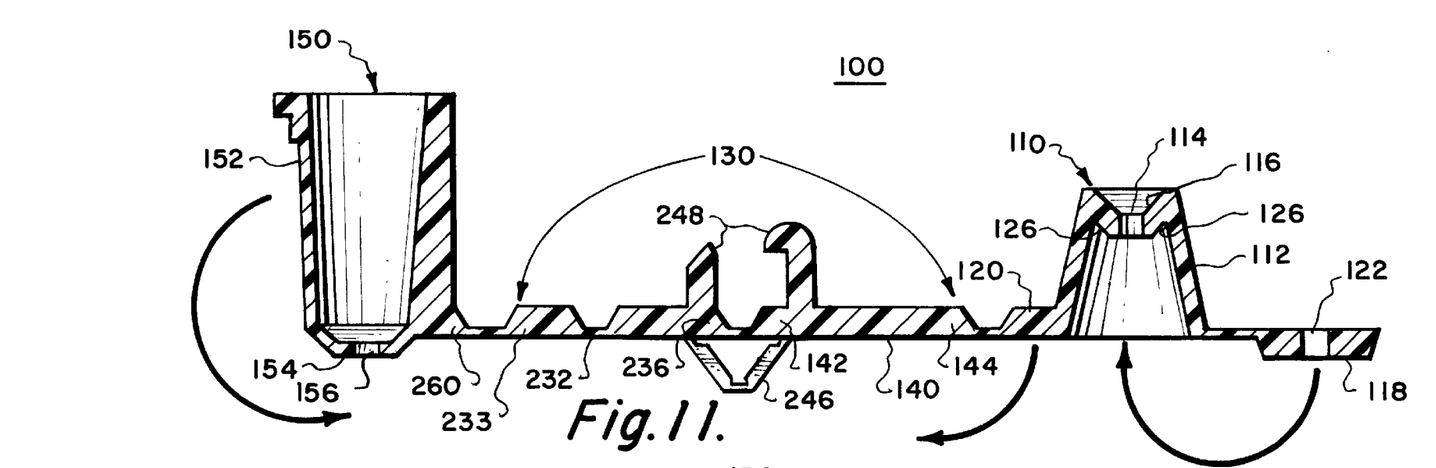
FIG. 11 is a cross-section at 11—11 of FIG. 10.

FIG. 11 shows how base cup 150 is rotated in preparation for needle passage through the base cup 150 and attachment to the syringe. FIG. 11 also shows how the enclosing member 118 is rotated to enclose the needle point cap 110 and how the needle point cap 110 is rotated in preparation for attachment to the syringe. The needle point cap 110 has the annular channel 126 located around the hole or bore 114 to help prevent the accidental re-emergence of the needle point through the hole 114 by capturing the needle point after the needle point cap 110 has been rotated about the needle point.

Figure 12:
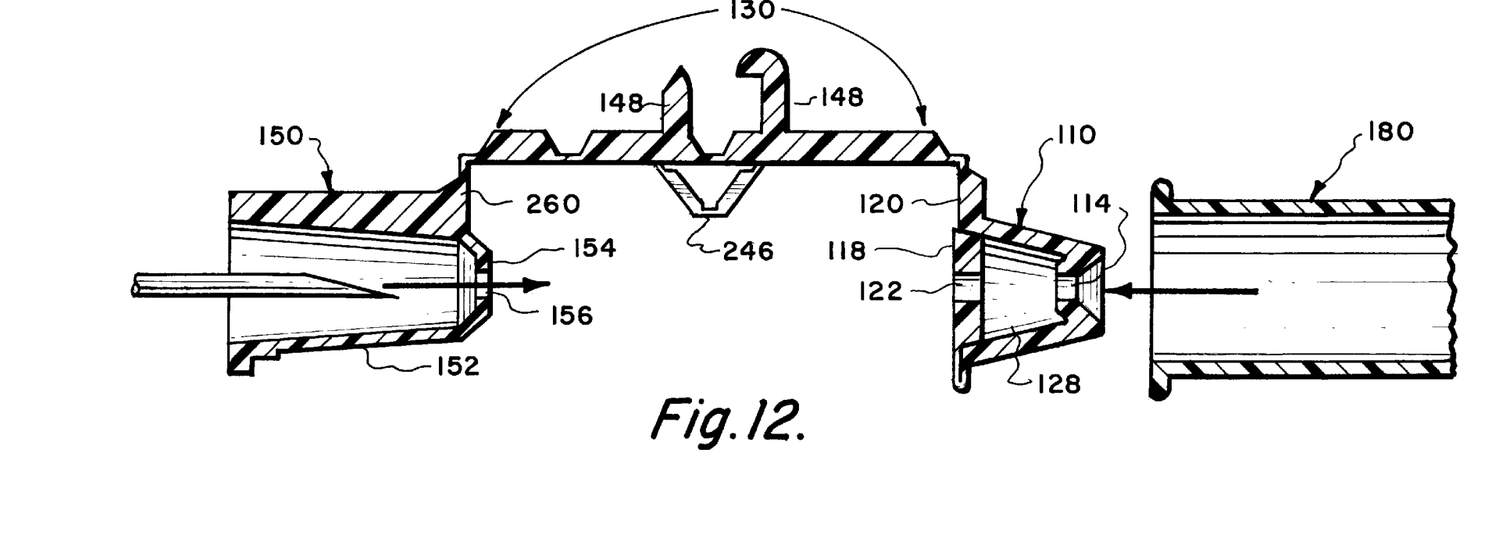
FIG. 12 is a cross-section at 11—11 of FIG. 10 prepared for attachment to a syringe.

FIG. 12 depicts the base cup 150 and the needle point cap 110 after rotation in preparation for installation on the syringe. It also shows the direction of needle insertion in preparation for attachment of the needle point guard safety cap assembly 100 to the syringe. FIG. 12 also depicts the enclosed needle point cap 110 having the chamber 128. FIG. 12 shows the needle sheath 180 being applied to the outside of the enclosed needle point cap 110.

FIG. 13 depicts the syringe with the needle point guard safety cap assembly 100 and the needle sheath 180 installed in a safe position is as the user would receive it prior to use. FIG. 14 shows the syringe with the needle sheath 180 removed and ready for use.

Subsequent to use, the user simply urges the folded collapsible extension 130 with his finger to overcome the snap-lock 246 and cause the needle point cap 110 to slide the length of the needle as shown in FIG. 15.

In this alternate embodiment, after the collapsible extension has been fully extended, it is further urged toward the needle shaft. In response to this urging, a force is applied to the lever arm so that its urging causes the needle point cap 110 to rotate about the needle point as shown in FIG. 16. Further urging causes sufficient deflection of the collapsible extension 130 so that the pair of interlockable protrusions 248 interlock. As shown in FIG. 16, the now interlocked protrusions 248 prevent the needle point cap 110 from sliding back up the needle shaft and exposing the needle point. It also ensures that the needle point cap 110 maintains its rotated or skewed position.

As can be seen in FIGS. 10 & 16, the snap-lock 246 does not interfere with the needle as the interlocking protrusions 248 are engaged. The snap-lock 246 simply extends on opposing sides of the needle shaft. The snap-lock could also be made to engage or clip to the needle shaft and thereby provide the means to secure the needle point cap 110 in the needle protective position.

FIGS. 17–20

FIGS. 17–20 show alternate embodiments of the base cup or syringe attachment member 150. Since syringes can come with or without needles attached and with varying attachment means, the needle point guard safety cap assembly 100 can be attached to the syringe 190 in any number of ways. It is also possible to have the needle molded or assembled as an integral part of the needle point guard safety cap assembly so that attachment of the syringe attachment member 150 to the syringe also attaches the needle to the syringe.

Typically syringe barrels 192 have a hub to which the needle hub or cone 194 can be coupled. It is presently preferred to have the syringe attachment member 150 frictionally engage the needle cone 194. In the presently preferred embodiment, slats 158 shown in FIGS. 1–9, engage the needle cone or hub 194. It could also be made to snap fit to the needle cone 194 or it could be directly coupled to the syringe barrel 192.

The syringe attachment member 150 could, of course, manually be held in place while the frame is being urged to release it and to slide the needle point cover 110. It is presently preferred, however, to have the syringe attachment member 150 engage the syringe 190 with sufficient force so that urging of the frame 130 does not cause it to dislodge from the syringe 190 slide down the needle.

While only several embodiments of the invention have been described, numerous modifications or other embodiments could be made without deviating from the invention thus described and in the following claims.

What I claim is:

1. A needle point cover assembly for securely covering and protecting the needle point of a syringe after the syringe has been used, comprising:

a needle point cover in the form of an elongated hollow member that is open at one end for receiving the needle therein, and at its other end is mostly enclosed by an end wall having a hole through which the needle can pass;

a lid enclosing upon the otherwise open end of the cover member, the lid also having a hole through which the needle may pass so that the needle may extend through both holes;

an extensible frame that is manually actuable for moving the cover member along the needle when the syringe is being readied for disposal; and means coupling one end of the extensible frame to the cover member and responsive to the actuation of the extensible frame for moving the cover member to where its end wall is beyond the extremity of the needle point;

the cover member then being supported by the hole in the lid and rotating about the lid hole until the needle point passes inside the enclosed end wall of the cover member into a protected position where it cannot pass through the cover member hole.

2. A needle point cover assembly as in claim 1 wherein the lid is pivotally secured to the cover member, and the cover member, lid, extensible frame and coupling means are integrally formed of plastic material.

3. A needle point cover assembly as in claim 1 which further comprises a manually actuated locking means for securing the cover member in the needle-protective position.

4. A needle point cover assembly as in claim 1 which further comprises a means for releasably locking the cover in a position distal from the point.

5. A needle point guard assembly comprising:

a) a syringe attachment member for attachment to a syringe;

b) a cup-shaped member for covering the point of a needle;

c) the cup-shaped member having a hole to allow the needle to pass through;

d) a lever arm projecting from the cup-shaped member;

e) a collapsible member having two end portions, the first of the two end portions being coupled to the syringe attachment member, the second end of the two end portions being coupled to the cup-shaped member for sliding the cup-shaped member along the needle, the lever arm being responsive to movement of the collapsible member when the needle point is located within the cup-shaped member such that the collapsible member causes the cup-shaped member to rotate about the needle point and preventing the needle point from passing through the hole; and f) the needle point guard assembly being integrally formed.

6. The needle point guard assembly of claim 5 wherein the collapsible member is attached directly to the lever arm.

7. The needle point guard assembly of claim 5 wherein the collapsible member is attached directly to the cup-shaped member.

8. The needle point guard assembly of claim 5 wherein the cup-shaped member further comprises an annular channel located around the hole for capturing the needle point within the rotated cup-shaped member.

9. The needle point guard assembly of claim 5 wherein the cup-shaped member further comprises an enclosing member for enclosing the otherwise open end of the cup-shaped member, the enclosing member having a hole for allowing the needle to pass through.

10. The needle point guard assembly of claim 5 which further comprises a means for releasably locking the cup-shaped member in a position distal from the point.

11. The needle point guard assembly of claim 10 wherein the means for releasably locking the cup-shaped member further comprises a protrusion on the syringe attachment member and a locking surface on the collapsible member such that the collapsible member can be releasably locked to the syringe attachment member and thereby retain the cup-shaped member distal from the needle point.

12. The needle point guard assembly of claim 5 wherein the cup-shaped member is adapted to receive a needle sheath thereby allowing the needle sheath to cover the needle when the cup-shaped member is distal from the needle point.

13. The needle point guard assembly of claim 5 further comprising a means for securing the rotated cup-shaped member in the rotated position.

14. The needle point guard assembly of claim 13 wherein the securing means comprises a clip extending from the collapsible member for surrounding the needle and securing the extended collapsible member to the needle thereby maintaining the rotated position of the cup-shaped member.

15. The needle point guard assembly of claim 13 wherein the securing means comprises a pair of interlockable protrusions extending from the collapsible member such that deflection of the extension toward the needle causes the protrusions to interlock thereby maintaining the rotated position of the cup-shaped member.

16. A needle point guard assembly comprising:
   a) a needle cap for containing the point of a needle comprising:
      (i) a circumferential wall, a top wall, and a bottom wall which define a chamber;
      (ii) the top wall and bottom wall of the needle point cap each containing a bore therethrough to allow passage of the needle, the top wall bore further allowing the needle point cap to skew with respect to the needle point while the needle extends through only the top wall bore, the needle point cap being capable of sliding the length of the needle;
      (iii) the circumferential wall having a lever arm attached thereto for skewing the needle point cap relative to the needle point; and
      (iv) the outer surface of the circumferential wall being shaped so as to receive a needle sheath thereby allowing the needle sheath to cover the needle when the needle point cap has been slid to a position distal from the point;
   b) a syringe attachment member for connecting the point guard assembly to a syringe; and
   c) a collapsible extension having two end portions, one end being flexibly connected to the syringe attachment member and the other end being flexibly connected to the needle point cap, the extension being capable of applying a force to the lever arm when the needle extends through only the top bore of the needle point cap so as to skew the needle point cap about the needle point.

17. The needle point guard assembly of claim 16 wherein the extension further comprises a pressure platform adjacent the needle point cap connection for urging the lever arm and thereby skewing the needle point cap.

18. The needle point guard assembly of claim 16 further comprising a means for securing the skewed needle point cap in the skewed position.

19. The needle point guard assembly of claim 18 wherein the securing means comprises a clip extending from the collapsible extension for surrounding the needle and securing the extended collapsible extension to the needle thereby maintaining the skewed position of the needle point cap.

20. The needle point guard assembly of claim 18 wherein the securing means comprises a pair of interlockable protrusions extending from the collapsible extension such that deflection of the extension toward the needle causes the protrusions to interlock thereby maintaining the skewed position of the needle point cap.

21. The needle point guard assembly of claim 16 which further comprises a means for releasably locking the needle point cap in a position distal from the point.

22. The needle point guard assembly of claim 21 wherein the means for releasably locking the needle point cap further comprises a protrusion on the syringe attachment member and a locking surface on the collapsible extension such that the collapsible extension can be releasably locked to the syringe attachment member and thereby retain the needle point cap distal from the needle point.

23. The needle point guard assembly of claim 16 wherein the collapsible extension is flexibly connected to the lever arm such that deflection of the extended extension toward the needle urges the lever arm and thereby skews the needle point cap.

24. The needle point guard assembly of claim 16 wherein the bore in the top wall is defined by at least partially beveled edges with the diameter of the bore decreasing as the bore opens to the chamber.

25. The needle point guard assembly of claim 16 wherein the needle point cap further comprises an annular channel defined within the chamber by the circumferential wall and the bottom wall.

26. The needle point guard assembly of claim 16 wherein the top wall of the needle point cap is flexibly attached to the circumferential wall such that top wall may be rotated about the attachment until it is seated within the circumferential wall thereby forming the chamber.

27. A needle point guard assembly comprising:
   a) a base cup comprising;
      (i) a circumferential wall with a bottom wall attached thereto for defining a cup,
      (ii) the cup being adapted to attach to a syringe,
      (iii) the bottom wall of the cup having a hole therethrough to allow passage of a needle,
      (iv) a pair of attachment arms extending outward from the circumferential wall near the base cup bottom wall, and
      (v) a locking nub protruding from the circumferential wall near the base cup bottom wall;
   b) a collapsible segmented extension having at least two segments comprising:
      (i) a wishbone segment having two arms and a base, the arms being flexibly attached to the base cup attachment arms such that the base cup can rotate about the axis formed by the attachment arms to wishbone connection; and (ii) a lower segment having upper and lower ends, the upper end being flexibly attached to the wishbone base, the lower segment having a locking ledge near the lower end for releasably locking the lower segment to the base cup locking nub when the segmented extension is collapsed and the lower segment is in a position adjacent the base cup; and c) a needle point cap flexibly connected to lower end of the lower segment, the needle point cap comprising:
  (i) a circumferential wall, a top wall, and a bottom wall which define a chamber; and
  (ii) the top wall and the bottom wall of the needle point cap each containing a bore therethrough to allow passage of the needle.

28. The needle point guard assembly of claim 27 wherein the lower segment of the segmented extension has a pressure platform interposed between the locking ledge and the lower end, and wherein the needle point cap further comprises a lever arm attached to the circumferential wall such that the pressure platform is in a cooperating relationship with the lever arm thereby causing the needle point cap to skew relative to the needle point when the lever arm is urged by the pressure platform and the needle extends through only the top of the needle point cap.

29. The needle point guard assembly of claim 27 wherein the bore in the top wall is defined by at least partially beveled edges with the diameter of the bore decreasing as the bore opens to the chamber.

30. The needle point guard assembly of claim 27 wherein the needle point cap further comprises an annular channel defined within the chamber by the circumferential wall and the bottom wall.

31. The needle point guard assembly of claim 27 wherein the lower segment further comprises at least one protruding clip for securing the extended extension to the needle and thereby maintaining the skewed position of the needle point cap and maintaining the position of the needle point cap relative to the base cup.

32. The needle point guard assembly of claim 27 wherein the needle point cap is capable of sliding the length of the needle and wherein the outer surface of the circumferential wall is adapted to receive a needle sheath thereby allowing the needle sheath to cover the needle when the needle point cap has been slid to a position distal from the point.

33. The needle point guard assembly of claim 27 wherein the top wall of the needle point cap is flexibly attached to the circumferential wall such that top wall may be rotated about the attachment until it is seated within the circumferential wall thereby forming the chamber.

* * * * *